US008059825B2

(12) United States Patent
Latzel

(10) Patent No.: US 8,059,825 B2
(45) Date of Patent: Nov. 15, 2011

(54) HEARING DEVICE SYSTEM WITH BINAURAL DATA LOGGING AND CORRESPONDING METHOD

(75) Inventor: Matthias Latzel, Eggolsheim (DE)

(73) Assignee: Siemens Audiologische Technik GmbH, Erlangen (DE)

( * ) Notice: Subject to any disclaimer, the term of this patent is extended or adjusted under 35 U.S.C. 154(b) by 1267 days.

(21) Appl. No.: 11/728,901

(22) Filed: Mar. 27, 2007

(65) Prior Publication Data

US 2007/0223753 A1 Sep. 27, 2007

(30) Foreign Application Priority Data

Mar. 27, 2006 (DE) ......................... 10 2006 014 022

(51) Int. Cl.
*H04R 25/00* (2006.01)
*A61N 1/00* (2006.01)

(52) U.S. Cl. .......... 381/23.1; 381/314; 381/315; 607/56

(58) Field of Classification Search ................. 381/23.1, 381/60, 314, 315; 455/41.2; 600/25; 607/56–57
See application file for complete search history.

(56) References Cited

U.S. PATENT DOCUMENTS

| | | | | |
|---|---|---|---|---|
| 4,972,487 | A | 11/1990 | Mangold | |
| 6,549,633 | B1 | 4/2003 | Westermann | |
| 6,768,802 | B1 | 7/2004 | Baechler | |
| 2004/0013280 | A1 | 1/2004 | Niederdrank | |
| 2004/0037442 | A1 | 2/2004 | Nielsen et al. | |
| 2004/0066944 | A1* | 4/2004 | Leenen et al. | 381/314 |
| 2004/0190739 | A1* | 9/2004 | Bachler et al. | 381/314 |
| 2004/0204921 | A1* | 10/2004 | Bye et al. | 702/189 |

FOREIGN PATENT DOCUMENTS

| | | | |
|---|---|---|---|
| DE | 100 48 354 | A1 | 5/2002 |
| DE | 10304648 | B3 | 8/2004 |
| EP | 1367857 | A1 | 12/2003 |
| EP | 1 414 271 | A2 | 4/2004 |
| EP | 1 445 982 | A1 | 8/2004 |
| WO | WO 99/43185 | A1 | 8/1999 |
| WO | 2007045276 | A1 | 4/2007 |

* cited by examiner

*Primary Examiner* — Curtis Kuntz
*Assistant Examiner* — Jesse Elbin

(57) ABSTRACT

The data of a hearing device system with two hearing devices are to be available in a more comfortable manner. To this end, provision is made for each of the two hearing devices to be equipped with a data acquisition facility, in order to acquire internal signal processing data and/or external data. The two data acquisition facilities and/or the hearing devices are designed to establish a wireless communication link. A synchronized data acquisition is possible in both hearing devices with the aid of this link. This binaural wireless data logging dispenses with the need for comparing the recording times (synchronization). A division of the recording onto two hearing devices enables storage capacity to be saved.

15 Claims, 1 Drawing Sheet

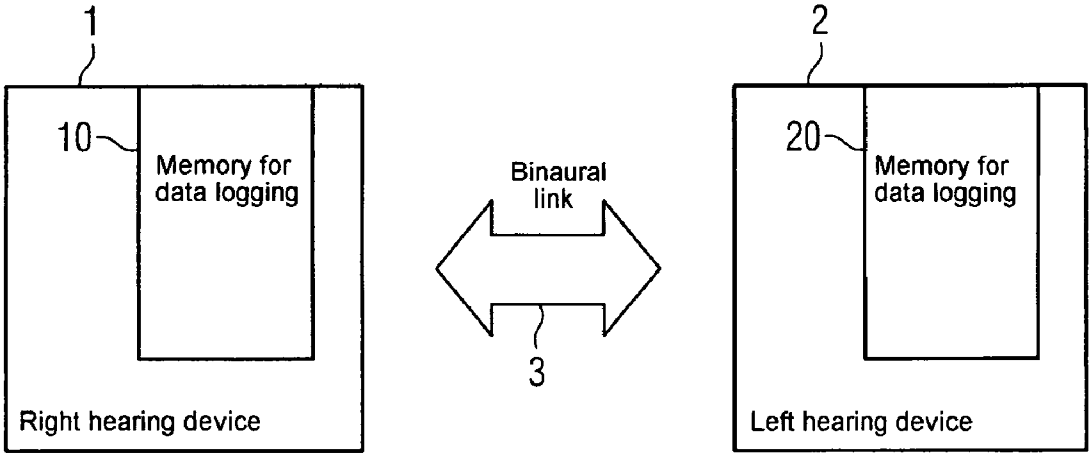
1
10
Memory for data logging
Right hearing device
Binaural link
3
2
20
Memory for data logging
Left hearing device

HEARING DEVICE SYSTEM WITH BINAURAL DATA LOGGING AND CORRESPONDING METHOD

CROSS REFERENCE TO RELATED APPLICATIONS

This application claims priority of German application No. 10 2006 014 022.2 filed Mar. 27, 2006, which is incorporated by reference herein in its entirety.

FIELD OF THE INVENTION

The present invention relates to a hearing device system having a first hearing device, which features a first data acquisition facility, in order to acquire internal signal processing data and/or external data, and a second hearing device, which features a second data recording facility, in order to likewise record internal signal processing data and/or external data. Furthermore, the present invention relates to a corresponding method for recording and/or acquiring data in a hearing device system.

BACKGROUND OF THE INVENTION

A hearing prosthesis having a data logging possibility is described in the patent application U.S. Pat. No. 4,972,487. The adjustments carried out by the user can thus be recorded. The recorded data is periodically read out and used for monitoring the device as well as for an improved initial adjustment for other patients. The prosthesis can comprise a remote controller and a data log memory can be made available in the remote controller together with a memory for control programs. The recorded data only refers however to that information which is available in the hearing device.

SUMMARY OF THE INVENTION

The object of the present invention consists in being able to better evaluate a hearing device system having two hearing devices in a data-related manner.

In accordance with the invention, this object is achieved by a hearing device system having a first hearing device, which features a first data acquisition facility in order to acquire internal signal processing data and/or external data, a second hearing device, which features a second data acquisition facility in order to acquire internal signal processing data and/or external data, with the two data acquisition facilities being designed to establish a wireless communication link, so that a synchronized data acquisition can be implemented in both hearing devices.

Furthermore, provision is made in accordance with the invention for a method for acquiring data in a hearing device system having a first and a second hearing device by means of acquiring first data in the first hearing device and simultaneously acquiring second data in the second hearing device, as well as wireless transmission of at least one part of the first data to the second hearing device and/or at least one part of the second data to the first hearing device and storing the data received from the transmission in the respective hearing device.

The acquisition and/or recording of data during the operation of a device is referred to as "data logging". A data logging of this type is also of interest in hearing devices, in order to be able to carry out adjustments dynamically or retroactively.

The first hearing device preferably features a storage facility for storage purposes and an evaluation facility for utilizing the acquired data of the second hearing device. A storage facility is thus not necessary on the one hand in the second hearing device. On the other hand, the entire storage capacity in both hearing devices can be reduced, since the entire memory is available to both hearing devices.

In accordance with a special embodiment of the present invention, the first data and the second data are compared in terms of content in the data acquisition facility, so that redundant data can be excluded from a storage process. The memory capacity of the entire hearing system can hereby be spared.

A bidirectional link between two hearing devices is advantageously established, so that a binaural item of information can be stored or utilized in both hearing devices. This means that each individual hearing device of the hearing device system can itself profit from the wireless communication.

It is advantageous in particular if the data acquisition is carried out as a function of information which is available in the first and/or second hearing device. For this reason, this is especially favorable, since a data acquisition and/or recording can then be interrupted, if one of the two hearing devices supplies a corresponding decision.

BRIEF DESCRIPTION OF THE DRAWINGS

The present invention is now described in more detail below with reference to the appended drawings, which reproduce a schematic diagram of a hearing device system according to the invention.

DETAILED DESCRIPTION OF THE INVENTION

The exemplary embodiments illustrated in more detail below represent preferred embodiments of the present invention.

The drawing illustrated in FIG. shows a hearing device system according to the invention having a first and/or right hearing device 1 and a second and/or left hearing device 2. The right hearing device 1 has an internal memory 10 for the data logging. The left hearing device 2 likewise has an internal memory 20 for the data logging. A binaural link 3 exists between both hearing devices 1, 2. This is realized as a wireless communication link. A preferably bidirectional data exchange between both hearing devices 1 and 2 is thus possible. Internal control data and also data which the respective hearing device has received from the outside can herewith be exchanged between the hearing devices 1, 2.

As the two hearing devices synchronously record and/or acquire data, a balancing of the recording times is no longer required to achieve a binaural data logging in order to process data binaurally, if necessary retrospectively. The fact that no or very little time information needs to be recorded means that storage capacity in turn is saved.

The data logging is carried out in each device 1, 2 or only in one of the two as a function of binaural information. This means that the data recorded during data logging can be immediately utilized in one or in both devices. The possibility thus exists for instance of triggering changes in the programming during the operation, said changes being based on the recordings. In this way, dynamically adapting hearing devices can be realized for instance.

In a concrete example, binaural input levels can be used for the decision as to whether or not a binaural change in the hearing device adjustment is to be registered. A further example for the use of binaural information consists here in that data is not then recorded in both hearing devices, if the hearing device wearer is using the telephone and one of the two hearing devices is set to the telephone mode. The recording could then basically be prevented if both hearing devices are set to different modes, since different hearing situations register in each instance. The reason for dispensing with the data logging lies in the fact that a comparison or an evaluation of the data of both hearing devices is relatively meaningless as a result of the different hearing situations.

Furthermore, the data logging of the entire hearing device system can be distributed on both devices, with information being transmitted if necessary from the left hearing device 2 to the right hearing device 1 or vice versa. Storage capacity can be saved by storing the data either on the left or right hearing device, since the same data does not need to be dually recorded. In this way, the recording can be carried out in a different manner according to the content of the data for instance. By way of example, data of a type in the right hearing device 1 and data of another type in the left hearing device 2 can thus be stored in this manner.

The binaural, wireless data logging is particularly advantageous if the information of both devices is already to be used during the operation. This is the case for instance if differences or ratios of recorded data of the two hearing devices are to be used for instance to control the hearing devices.

The binaural data logging dispenses with the need for a retrospective binaural evaluation, to synchronize the recordings of both hearing devices. Instead, the recorded binaural information is available in an immediately synchronized form and can be utilized without a time delay. As already mentioned above, changes to the programming of the devices can be initiated immediately during the operation of the hearing devices, on the basis of the binaural information.

The invention claimed is:

1. A hearing device system, comprising:

a first hearing device comprising a first data logging unit for recording a first adjustment to the first hearing device;

a second hearing device comprising a second data logging unit for recording a second adjustment to the second hearing device; and a communication link that links the first and the second data logging units for synchronizing the first and the second adjustments so that a synchronized adjustment is implemented in the first and the second hearing devices, wherein the first or the second hearing device further comprises a storage unit that stores the first and the second adjustments, and wherein a content of the first adjustment is compared with a content of the second adjustment in the first or the second data logging unit to avoid a redundant data stored in the storage unit.

2. The hearing device system as claimed in claim 1, wherein the first or the second hearing device further comprises an evaluation unit that evaluates the first and the second adjustments.

3. The hearing device system as claimed in claim 1, wherein the communication link is a bidirectional link and a binaural information is stored or evaluated in the first or the second hearing device.

4. The hearing device system as claimed in claim 1, wherein the first and the second adjustments are recorded as a function of information that is available in the first or the second hearing device.

5. The hearing device system as claimed in claim 1, wherein the communication link is a wireless communication link.

6. A method for adjusting a hearing device system having a first and a second hearing device, comprising:

acquiring a first adjustment data in the first hearing device;

simultaneously acquiring a second adjustment data in the second hearing device;

transmitting the first adjustment data to the second hearing device via a communication link;

synchronizing the first adjustment data with the second adjustment data to generate a synchronized adjustment data;

adjusting the hearing device system based on the synchronized adjustment data, and storing the first and the second adjustment data in the second hearing device, wherein the first adjustment data is compared with the second adjustment to avoid storing a redundant adjustment data.

7. The method as claimed in claim 6, wherein the second adjustment data is transmitted to the first hearing device via the communication link.

8. The method as claimed in claim 6, wherein the communication link is a bidirectional link and a binaural information is stored or evaluated in the first or the second hearing device.

9. The method as claimed in claim 6, wherein the first and the second adjustment data are recorded as a function of information that is available in the first or the second hearing device.

10. The method as claimed in claim 6, wherein the communication link is a wireless communication link.

11. A method for adjusting a hearing device system having a first and a second hearing device, comprising:

acquiring a first adjustment data in the first hearing device;

simultaneously acquiring a second adjustment data in the second hearing device;

transmitting the second adjustment data to the first hearing device via a communication link;

synchronizing the second adjustment data with the first adjustment data to generate a synchronized adjustment data; and adjusting the hearing device system based on the synchronized adjustment data, wherein the first and the second adjustment data are stored in the first hearing device and compared with each other to avoid storing a redundant adjustment data.

12. The method as claimed in claim 11, wherein the first adjustment data is transmitted to the second hearing device via the communication link.

13. The method as claimed in claim 11, wherein the communication link is a bidirectional link and a binaural information is stored or evaluated in the first or the second hearing device.

14. The method as claimed in claim 11, wherein the first and the second adjustment data are recorded as a function of information that is available in the first or the second hearing device.

15. The method as claimed in claim 11, wherein the communication link is a wireless communication link.

* * * * *